(12) United States Patent
Roy et al.

(10) Patent No.: US 8,992,994 B2
(45) Date of Patent: Mar. 31, 2015

(54) TOPICAL PHARMACEUTICAL COMPOSITIONS CONTAINING NANODROPLETS FOR THE TREATMENT PSORIASIS

(75) Inventors: Sunilendu Bhushan Roy, Ahmedabad (IN); Jay Shantilal Kothari, Ahmedabad (IN); Shafiq Sheikh, Ahmedabad (IN); Jitendra Dasharathlal Patel, Ahmedabad (IN); Jinesh Suresh Pancholi, Ahmedabad (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 13/880,519

(22) PCT Filed: Oct. 18, 2011

(86) PCT No.: PCT/IN2011/000716
§ 371 (c)(1),
(2), (4) Date: Jun. 5, 2013

(87) PCT Pub. No.: WO2012/053007
PCT Pub. Date: Apr. 26, 2012

(65) Prior Publication Data
US 2013/0273172 A1    Oct. 17, 2013

(30) Foreign Application Priority Data
Oct. 21, 2010   (IN) .......................... 2924/MUM/2010

(51) Int. Cl.
| | | |
|---|---|---|
| A61K 9/107 | (2006.01) | |
| A61K 31/60 | (2006.01) | |
| A61K 31/573 | (2006.01) | |
| A61K 9/00 | (2006.01) | |
| A61K 47/44 | (2006.01) | |
| B82Y 5/00 | (2011.01) | |

(52) U.S. Cl.
CPC ............... *A61K 9/107* (2013.01); *A61K 9/0014* (2013.01); *A61K 9/1075* (2013.01); *A61K 31/573* (2013.01); *A61K 31/60* (2013.01); *A61K 47/44* (2013.01); *B82Y 5/00* (2013.01)

USPC ............................ 424/502; 514/163; 424/489

(58) Field of Classification Search
None
See application file for complete search history.

(56) References Cited

U.S. PATENT DOCUMENTS

| | | | | |
|---|---|---|---|---|
| 2003/0219465 | A1* | 11/2003 | Gidwani et al. | 424/401 |
| 2006/0110415 | A1* | 5/2006 | Gupta | 424/401 |
| 2007/0036831 | A1* | 2/2007 | Baker | 424/400 |
| 2009/0324727 | A1* | 12/2009 | Foguet Roca | 424/489 |

FOREIGN PATENT DOCUMENTS

| | | |
|---|---|---|
| EP | 1 364 642 | 11/2003 |
| WO | WO 2008/077641 | 7/2008 |

OTHER PUBLICATIONS

Chemical Book Apr. 9, 2009.*
International Preliminary Report on Patentability mailed May 2, 2013 for Application No. PCT/IN2011/000716.
International Search Report for PCT/IN2011/000716 mailed Apr. 5, 2012.
Written Opinion of the International Searching Authority mailed Apr. 5, 2012.
M. Fontanaet al., "Nanoencapsulation as a Way to Control the Release and to Increase the Photostability of Clobetasol Propionate; Influence of the Nanostructured System", Journal of Biomedical Nanotechnology, vol. 5, No. 3, Jun. 2009, pp. 254-263.
M. Labwohl et al., "The Role of Salicylic Acid in the Treatment of Psoriasis", International Journal of Dermatology, vol. 38, No. 1, Jan. 1, 1999, pp. 16-24.
S. Khandavilli et al., "Nanoemulsions as Versitile Formulations for Paclitaxel Delivery: Peroral and Dermal Delivery Studies in Rats", Journal of Investigative Dermatology, vol. 127, No. 1, Jan. 2007, pp. 154-162.

* cited by examiner

*Primary Examiner* — Scott Long
*Assistant Examiner* — Sarah Alawadi
(74) *Attorney, Agent, or Firm* — Nixon & Vanderhye P.C.

(57) ABSTRACT

The present invention relates to stable topical pharmaceutical compositions for the treatment of psoriasis. Disclosed are in particular nonoemulsions comprising nano size droplets of one or more anti-psoriasis agents, e.g. clobetasol and/or salicylic acid. These compositions exhibit greater permeability, and improved bioavailability. The invention also relates to processes for the preparation of such compositions.

7 Claims, No Drawings

TOPICAL PHARMACEUTICAL COMPOSITIONS CONTAINING NANODROPLETS FOR THE TREATMENT PSORIASIS

This application is the U.S. national phase of International Application No. PCT/IN2011/000716 filed 18 Oct. 2011 which designated the U.S. and claims priority to IN 2924/MUM/2010 filed 21 Oct. 2010, the entire contents of each of which are hereby incorporated by reference.

FIELD OF THE INVENTION

The present invention relates to stable topical pharmaceutical compositions for the treatment of psoriasis. These compositions exhibit greater permeability, and improved bioavailability. The invention also relates to processes for the preparation of such compositions.

BACKGROUND OF THE INVENTION

Psoriasis is a chronic, non-infectious disease that affects mainly the skin. It is currently suspected to be autoimmune in origin. It commonly causes red, scaly patches to appear on the skin, although some patients have no dermatological symptoms. The scaly patches caused by psoriasis, called psoriatic plaques, are areas of inflammation and excessive skin production. Skin rapidly accumulates at these sites and takes on a silvery-white appearance. The disorder is a chronic recurring condition that varies in severity from minor localized patches to complete body coverage. The cause of psoriasis is not exact, but it is believed to have a genetic component and it can be triggered by a prolonged injury to the skin known as 'Koebner phenomenon'.

Psoriasis is seen worldwide, in all races, and both sexes. Although psoriasis can be seen in people of any age, from babies to seniors, most commonly patients are first diagnosed in their early adult years.

Patients with more severe psoriasis may have social embarrassment, job stress, emotional distress, and other personal issues because of the appearance of their skin.

There are many treatments available, but because of its chronic recurrent nature, psoriasis is a challenge to treat. Amongst various treatments, topical treatment is widely used for the management of psoriasis. Ointment and creams containing coal tar, dithranol (anthralin), corticosteroids like desoximetasone (Topicort), fluocinonide, vitamin $D_3$ analogues (for example, calcipotriol), and retinoids are routinely used.

Clobetasol propionate is a corticosteroid used to treat various skin disorders including eczema and psoriasis. Clobetasol belongs to US Class I (Europe: class IV), i.e. super potent of the corticosteroids, making it one of the most potent therapeutic regimen available for psoriasis. It comes in ointment, cream, gel, emulsion, aerosol foam, shampoo presentations. However, use of clobetasol is limited substantially due to its side effects such as burning sensation, itching, dryness and irritation.

U.S. Patent Publication No. 20060239929 discloses a method for treating psoriasis, by spraying onto the skin with psoriasis daily for at least 4 weeks a pharmaceutical composition containing an effective amount of clobetasol propionate. A preferred pharmaceutical composition contains clobetasol propionate, ethyl alcohol, isopropyl myristate, and anionic surfactant.

U.S. Patent Publication No. 20090047359 discloses an ointment for treating and curing skin diseases of human beings such as psoriasis, dermatitis, acne, herpes and fungi, consisting of a composition obtained based on ingredients such as white petrolatum, clobetasol propionate, distilled water, rosemary honey, virgin olive oil, white precipitate mercury chloride, salicylic acid, and gentian violet.

U.S. Pat. No. 5,629,021 relates to micellar nanoparticles and methods of their production.

U.S. Pat. No. 5,894,019 discloses topical compositions comprising lipid and essentially free of emulsifiers and surfactants.

European Patent No. EP 506197 B1 discloses an aqueous suspension of solid lipid nanoparticles for topical use.

European Patent No. EP 671903 B1 discloses topical compositions in the form of submicron oil spheres.

Most of the topical preparations contain vehicles comprising permeation enhancers, solvents, and high amount of surfactants to achieve these goals. But use of these agents is harmful, especially in chronic application, as many of them are irritants.

Therefore, there exists a need to develop such topical preparations of anti-psoriatic agents which does not involve use of such agents as described above to facilitate drug permeation through the skin, and still leads to excellent photostability, greater permeability, and improved bioavailability resulting in enhanced therapeutic activity.

The compositions of the invention overcome all the commonly encountered problems as exemplified above.

SUMMARY OF THE INVENTION

In one general aspect there is provided a stable pharmaceutical composition comprising nano size droplets of one or more anti-psoriatic agents or salts, esters thereof.

In one general aspect there is provided a stable pharmaceutical composition comprising nano size droplets of clobetasol or salts, esters thereof.

In another general aspect there is provided a stable pharmaceutical composition comprising combination of clobetasol and salicylic acid or salts, esters thereof, wherein either clobetasol or salts thereof or both clobetasol and salicylic acid or salts, esters thereof or its salt are present in the form of nano size droplets.

In another general aspect there is provided a stable topical pharmaceutical composition comprising nano size droplets of one or more anti-psoriatic agents or salts, esters thereof, wherein the amount of anti-psoriatic agents or salt thereof in the composition ranges from about 0.01% to about 8.0% w/w of the composition.

In another general aspect there is provided a stable topical pharmaceutical composition comprising nano size droplets of clobetasol or salts, esters thereof, wherein the amount of clobetasol or salt, esters thereof in the composition ranges from about 0.01% to about 0.5% w/w of the composition.

In another general aspect there is provided a stable topical pharmaceutical composition comprising nano size droplets of one or more anti-psoriatic agents or salts, esters thereof, wherein said composition comprises oil in amount ranging from about 5 to about 25% w/w of the composition.

In another general aspect there is provided a stable topical pharmaceutical composition comprising nano size droplets of one or more anti-psoriatic agents or salts, esters thereof, wherein said composition comprises one or more emulsifier/s in amount ranging from about 0.1 to about 10% w/w of the composition.

In another general aspect there is provided a stable topical pharmaceutical composition comprising nano size droplets of one or more anti-psoriatic agents or salts, esters thereof, wherein said composition comprises one or more emulsifier/s and oil in the weight ratio ranging from about 0.1:20 to about 0.1:1.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

In another general aspect there is provided a stable topical pharmaceutical composition comprising nano size droplets of one or more anti-psoriatic agents or salts, esters thereof, wherein the composition is characterized by enhanced onsite delivery, permeability characteristics and/or bioavailability.

In another general aspect there is provided a stable topical pharmaceutical composition comprising nano size droplets of one or more anti-psoriatic agents or salts, esters thereof, wherein the composition retains at least 80% potency of said agent after 3 months at 40° C. and 75% relative humidity.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

D90 particle size of droplets of anti-psoriatic agents or salts, esters thereof in the compositions of the invention is less than 500 nm, preferably less than 300 nm, more preferably less than 100 nm.

In another general aspect there is provided a method of improving the onsite delivery of one or more anti-psoriatic agents or salts, esters thereof by providing a topical pharmaceutical composition comprising nano size droplets of one or more anti-psoriatic agents or salts, esters thereof.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

In another general aspect, there is provided a stable pharmaceutical composition comprising one or more anti-psoriatic agents or salts, esters thereof prepared by a process comprising:
a) combining an oily phase comprising one or more anti-psoriatic agents or salts, esters thereof along with other pharmaceutically acceptable excipients with an aqueous phase to form an emulsion;
b) reducing the particle size of emulsion of step a) to a droplet size having $D_{90}$ particle size of less than 500 nm; and
c) mixing other pharmaceutically acceptable excipients to the emulsion obtained in step b) and converting it into a suitable finished dosage form.

Embodiments of the pharmaceutical composition may include one or more of the following features. The pharmaceutical composition may further include one or more pharmaceutically acceptable excipients. For example, the pharmaceutically acceptable excipients may include one or more of oils, lipids, stabilizers, surfactants, initiators, thickening agents, and the like.

In another general aspect there is provided a method of treating psoriasis comprising topical application of the pharmaceutical composition comprising nano size droplets of one or more anti-psoriatic agents or salts, esters thereof.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

The details of one or more embodiments of the invention are set forth in the description below. Other features, objects and advantages of the invention will be apparent from the description and claims.

DETAILED DESCRIPTION OF THE INVENTION

The inventors of the invention have surprisingly found that when one or more pharmaceutically active agents useful for management of psorisis are formulated into nano size droplets in pharmaceutically acceptable emulgel (emulsion gel) system which includes optimized ratios of oils and/or emulsifiers, the composition exhibits enhanced therapeutic effect and it also exhibits excellent storage stability. Further, such compositions have enhanced permeability characteristics and/or improved bioavailability.

Moreover, the composition of the invention results in immediate and sustained action and covers large surface area with less quantity and good spreadability, non-irritant to skin and mucous membranes, reduced frequency of application leading to improved patient compliance and offers cosmetic benefits like non-stickiness, and non-greasy feel.

Thus, the present invention provides a stable topical pharmaceutical composition comprising one or more pharmaceutically active agents useful for management of psoriasis wherein the said agents are present in the form of nano size droplets.

In a preferred embodiment, the nano size droplets of anti-psoriatic agent or salts, esters thereof posses a $D_{90}$ particle size of less than about 500 nm.

In a preferred embodiment, the nano size droplets of anti-psoriatic agent or salts, esters thereof posses a $D_{90}$ particle size of less than about 400 nm.

In a preferred embodiment, the nano size droplets of anti-psoriatic agent or salts, esters thereof posses a $D_{90}$ particle size of less than about 300 nm.

In a preferred embodiment, the nano size droplets of anti-psoriatic agent or salts, esters thereof posses a $D_{90}$ particle size of less than about 200 nm.

In a preferred embodiment, the nano size droplets of anti-psoriatic agent or salts, esters thereof posses a $D_{90}$ particle size of less than about 100 nm.

The anti-psoriatic agents useful for the purpose of the present invention may be selected from, but not limited to topical steroids such as Clobetasol, Mometasone, Triamcinolone, Flucinonide, Desoximetasone, Alclometasone, Hydrocortisone, Diflorasone, Flurandrenolide, Amcinonide, Prednicarbate, Desonide, Halcinonide, Clocortolone; Psoralens such as Methoxsalen; Antipsoriatics such as Acitretin; Immunosuppressive agents such as Alefacept, Cyclosporin; Glucocorticoid such as Triamcinolone, Prednisone; Topical antipsoriatics such as Calcipotriene, Anthralin, Resorcinol, Betamethasone, Calcipotriene, Tazarotene; Antirheumatics, TNF inhibitors such as Etanercept, Adalimumab, Efalizumab, Ustekinumab; Topical emollients such as Ammonium lactate, Urea; Corticotropin and coal tar.

In a preferred embodiment, the composition of the present invention comprises clobetasol or salts, esters thereof.

The composition of the present invention exhibits excellent storage stability and retains at least 80% potency of, antipsoriatic agent when stored for at least three months at 40° C. and 75% relative humidity.

The invention further contemplates composition comprising combination of clobetasol or salts, esters there in the form of nano sized droplets and salicylic acid. or salts, esters thereof.

In a further embodiment, the composition of the present invention may comprise nano size droplets of clobetasol and salicylic acid or salts, esters thereof. The composition also retains at least 80% potency of both clobetasol and salicylic acid or salts, esters thereof when stored for at least three months at 40° C. and 75% relative humidity.

The amount of anti-psoriatic agent or salts, esters thereof in the composition may range from about 0.01% to about 8.0% w/w (based on 100% total weight of the composition).

In an embodiment, the composition comprises about 0.01% to about 0.5% w/w of clobetasol or salts, esters thereof (based on 100% total weight of the composition).

In a further embodiment, the composition comprises about 4.0% to about 8.0% w/w of salicylic acid or salts, esters thereof (based on 100% total weight of the composition).

The composition of the present invention further comprises one or more pharmaceutically acceptable excipients selected from, but not limited to lipids, oils, emulsifiers, stabilizers, initiators, pH adjusting agents, emollients, humectants, preservatives, antioxidants and chelating agents.

Suitable lipids which can be used include one or more of hydrocarbons, fatty alcohols, fatty acids, glycerides or esters of fatty acids with $C_1$-$C_{36}$ alkanols. Hydrocarbons may include paraffin or petroleum jelly. Fatty alcohols may include decanol, dodecanol, tetradecanol, hexadecanol or octadecanol. Fatty acids may include $C_6$-$C_{24}$ alkanoic acids such as hexanoic acid, octanoic acid, decanoic acid, dodecanoic acid, tetradecanoic acid, hexadecanoic acid, octadecanoic acid, unsaturated fatty acids such as oleic acid and linoleic acid. Glycerides may include olive oil, castor oil, sesame oil, caprylic/capric acid triglyceride or glycerol mono-, di- and tri-esters with palmitic and/or stearic acid. Esters of fatty acids may include $C_1$-$C_{36}$ alkanols such as beeswax, carnauba wax, cetyl palmitate, lanolin, isopropyl myristate, isopropyl stearate, oleic acid decyl ester, ethyl oleate and $C_6$-$C_{12}$ alkanoic acid esters and the like.

Suitable oils may include one or more of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane, sunflower seed oil, tricaprylin (1,2,3 trioctanoyl glycerol) and wheat germ oil and the like. The preferred quantity of oil used is in the range of about 5 to about 25% w/w, and more preferably in the range of about 5% to about 20% w/w of the composition.

Suitable emulsifiers may include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly(oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), polymers or copolymers of acrylic acid (commercially available as Carbopol®), phenoxypolyethoxyethanols and polymers thereof such as Triton®, Poloxamer®, Spans®, Tyloxapol®, different grades of Brij, sodium dodecyl sulfate and the like. The preferred quantity of the emulsifiers used is in the range of about 0.1% to about 10% w/w of the composition.

In a preferred embodiment, the ratio of emulsifier or surfactant to oil in the pharmaceutical composition of the present invention ranges from about 0.1:20 to about 0.1:1, preferably about 0.1:10 to about 0.1:1.

Suitable pH adjusting agents which can be used include one or more of organic or inorganic acids and bases including sodium hydroxide, potassium hydroxide, ammonium hydroxide, phosphate buffers, citric acid, acetic acid, fumaric acid, hydrochloric acid, malic acid, nitric acid, phosphoric acid, propionic acid, sulfuric acid, tartaric acid and the like. In an embodiment, the pH of the composition of the invention may range from about 4.5 to about 7.0, and preferably from 5.0 to about 6.5.

Suitable emollients which can be used include one or more of caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea and the like.

Suitable preservatives which can be used include one or more of phenoxyethanol, parabens (such as methylparaben and propylparaben), propylene glycols, sorbates, urea derivatives (such as diazolindinyl urea), and the like.

Suitable antioxidants which can be used include one or more of ascorbic acid, alpha-tocopherol (vitamin-E), butylated hydroxyanisole (BHA), butylated hydroxytoluene (BHT), glutathione, sodium metabisulphite and the like. The amount of antioxidant may range from about 0.05% to about 1.0% w/w of the total weight of the composition.

Suitable humectants which can be used include one or more of propylene glycol, glycerin, butylene glycol, sorbitol, triacetin and the like.

Suitable chelating agents which can be used include one or more of disodium EDTA, edetate trisodium, edetate tetrasodium, diethyleneamine pentaacetate and the like.

Suitable stabilizers may include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly(oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the stabilizer or surfactant used is in the range of 1 to 10% w/w of the composition.

Suitable initiators may include one or more of alcohols like $C_1$-$C_{12}$ alcohols, diols and triols, glycerol, methanol, ethanol, propanol, octanol, and the like. The amount of initiator may range from about 3.0% to about 7.0% w/w of the total weight of the composition.

The composition of the invention may be prepared by a) combining an oily phase comprising one or more pharmaceutically active agents useful for management of psorisis along with other pharmaceutically acceptable excipients with an aqueous phase to form an emulsion; b) reducing the particle size of emulsion of step a) to a droplet size having $D_{90}$ particle size of 500 nm; and c) mixing other pharmaceutically acceptable excipients to emulsion obtained in step b) and converting it into a suitable finished dosage form.

In an embodiment, the stable pharmaceutical composition comprising one or more pharmaceutically active agents useful for management of psoriasis is prepared by a process comprising:
- a) combining an oily phase comprising one or more pharmaceutically active agents useful for management of psoriasis along with other pharmaceutically acceptable excipients with an aqueous phase to form an emulsion;
- b) reducing the particle size of emulsion of step a) to a droplet size having $D_{90}$ particle size of about 500 nm; and
- c) mixing other pharmaceutically acceptable excipients to the emulsion obtained in step b) and converting it into a suitable finished dosage form.

In a further embodiment, the process of preparing a stable pharmaceutical composition comprising nano size droplets of one or more anti-psoriatic agents or salts, esters thereof comprising steps of:
- a) preparing a hydroalcoholic phase of one or more pharmaceutically active agents useful for management of psorisis with one or more alcohol, emulsifier and thickening agent.
- b) mixing the above hydroalcoholic phase was mixed with one or more oil and water.
- c) homogenizing the blend of step (b) to reduce the droplet size to $D_{90}$ particle size of less than 500 nm to form a nano emulsion and optionally, adding the aqueous dispersion of thickening agent to the above nano emulsion to get the nanogel.

The nano size droplets may be produced with reciprocating syringe instrumentation, continuous flow instrumentation, high speed mixing or high pressure homogenization. However, it will appreciated to the person skilled in the art any known method of reducing the size of droplet may be adopted to serve the purpose of the present invention.

Small droplets of the nano emulsion may be formed by passing the emulsion through a homogeniser under different pressures ranging from 3,500-21,500 psi. The emulsion may be passed between 4-5 times under the same conditions to get a final $D_{90}$ droplet size of about 500 nm. The nano droplets formed may be filtered through 0.2 to 0.4 micron filter.

The gel base may be used in the present invention to form a gel matrix for the preparation of nanogel from nanoemulsion. The gel base comprises of one or more of thickening agents.

Suitable thickening agents may include one or more of cellulose polymer, a carbomer polymer, a carbomer derivative, a cellulose derivative, polyvinyl alcohol, poloxamers, polysaccharides and the like.

Suitable dosage form of the invention may include cream, gel, ointment, lotion, and emulsion.

In a preferred embodiment, the composition of the invention is in the form of gel.

The present invention provides a method of improving therapeutic efficacy of the anti-psoriatic agent by providing a pharmaceutical composition comprising nano size droplets of one or more anti-psoriatic agents or salts, esters thereof.

The present invention also provides a method of improving the onsite delivery of one or more pharmaceutically active agents in management of psoriasis by providing a pharmaceutical composition comprising nano size droplets of one or more anti-psoriatic agent or salts thereof.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

EXAMPLE 1

Clobetasol Propionate and Salicylic Acid Lotion

TABLE 1

| Ingredients | % w/w |
|---|---|
| Clobetasol Propionate | 0.01-0.5 |
| Salicylic Acid | 4-8 |
| Lactic Acid | 1-5 |
| Polysorbate 80 | 1-5 |
| Alcohol | 3-7 |
| Glycerine | 3-7 |
| Soyabean Oil | 7-12 |
| BHT | 0.05-0.5 |
| Carbopol 980 | 0.5-3 |
| Sodium Hydroxide I.P. | Q.S |
| Purified Water IP | Q.S |

Procedure: Clobetasol propionate and BHT were mixed with alcohol, salicylic acid, sodium hydroxide, water, lactic Acid, polysorbate 80, glycerine and soyabean Oil. The resulting blend was homogenized to reduce the droplet size to $D_{90}$ particle size of about 250 nm with the help of high pressure homogenization to get the nano emulsion. Sodium hydroxide solution was added to Carbopol 980 solution to adjust suitable pH which was then finally mixed with nano emulsion to get lotion.

EXAMPLE 2

Clobetasol Propionate and Salicylic Acid Lotion

TABLE 2

| Ingredients | % w/w Composition |
|---|---|
| Clobetasol Propionate | 0.01-0.5 |
| Salicylic Acid | 3-8 |
| Lactic Acid | 1-5 |
| Polysorbate 80 | 1-5 |
| Alcohol | 3-7 |
| Glycerine | 3-7 |
| Soyabean Oil | 7-10 |
| BHT | 0.001-0.5 |
| HEC (250 HHX) | 0.5-3 |
| Sodium Hydroxide I.P. | Q.S |
| Purified Water IP | Q.S |

Procedure: Clobetasol propionate and BHT were mixed in alcohol, salicylic acid, sodium hydroxide, water, polysorbate 80, glycerine and soyabean oil were. The resulting blend was homogenized to reduce the droplet size to $D_{90}$ particle size of about 250 nm by high pressure homogenization to get the nano emulsion. Sodium hydroxide solution was slowly added to aqueous dispersion of HEC and lactic acid to adjust the desired pH. The aqueous dispersion of HEC was then mixed with nano emulsion to get lotion.

EXAMPLE 3

Clobetasol Propionate and Salicylic Acid Lotion

TABLE 3

| Ingredients | % w/w Composition |
|---|---|
| Clobetasol Propionate | 0.01-0.1 |
| Salicylic Acid | 4-8 |
| Polysorbate 80 | 1-5 |
| Alcohol | 3-7 |
| Glycerine | 3-7 |
| Soyabean Oil | 7-11 |
| BHT | 0.001-0.1 |
| HEC (250 HHX) | 0.5-3 |
| Sodium Hydroxide I.P. | Q.S |
| Purified Water IP | Q.S |

Procedure: Clobetasol propionate and BHT were mixed with alcohol, salicylic acid, sodium hydroxide, water, polysorbate 80, glycerine and soyabean oil. The resulting blend was homogenized to reduce the droplet size to $D_{90}$ particle size of about 250 nm by high pressure homogenization to get the nano emulsion. The aqueous dispersion of HEC was mixed with nano emulsion to get lotion.

EXAMPLE 4

Salicylic Acid Lotion

TABLE 4

| Ingredients | % w/w |
|---|---|
| Salicylic Acid | 4-8 |
| Polysorbate 80 | 1-5 |
| Alcohol | 3-7 |
| Glycerine | 3-7 |
| Soyabean Oil | 7-12 |
| BHT | 0.001-0.1 |
| Carbopol 980 NF | 1-4 |
| Sodium Hydroxide I.P. | Q.S |
| Purified Water IP | Q.S |

Procedure: BHT was mixed with alcohol, salicylic acid, sodium hydroxide, water, polysorbate 80, glycerine and soyabean oil. The resulting blend was homogenized to reduce the droplet size to $D_{90}$ particle size of about 250 nm by high pressure homogenization to get the nano emulsion. The aqueous dispersion of carbomer was mixed with nano emulsion followed by addition of sodium hydroxide Solution to form a lotion.

EXAMPLE 5

Salicylic Acid Lotion

TABLE 5

| Ingredients | % w/w |
|---|---|
| Salicylic Acid | 4-8 |
| Polysorbate 80 | 1-5 |
| Alcohol | 3-7 |
| Glycerine | 3-7 |
| Soyabean Oil | 7-12 |
| BHT | 0.001-0.1 |
| HEC (250 HHX) | 0.5-3 |
| Sodium Hydroxide I.P. | Q.S |
| Purified Water IP | Q.S |

Procedure: BHT was mixed with alcohol, salicylic acid, sodium hydroxide, water, polysorbate 80, glycerine and soyabean oil. The resulting blend was homogenized to reduce the droplet size to $D_{90}$ particle size of about 250 nm with the help of high pressure homogenization to get the nano emulsion. The aqueous dispersion of HEC was mixed with nano emulsion to form a lotion.

EXAMPLE 6

Clobetasol Propionate and Salicylic Acid Lotion

TABLE 6

| Ingredients | % w/w |
|---|---|
| Clobetasol Propionate | 0.01-0.1 |
| Salicylic Acid | 1-5 |
| Polysorbate 80 | 1-5 |
| Alcohol | 3-7 |
| Glycerine | 3-7 |
| Soyabean Oil | 7-12 |
| BHT | 0.001-0.1 |
| Carbopol 980 | 0.5-3 |
| Sodium Hydroxide | Q.S |
| Purified Water | Q.S |

Procedure: Clobetasol propionate and BHT were dissolved with alcohol, salicylic acid, sodium hydroxide, water, polysorbate 80, glycerine and soyabean oil. The resulting blend was homogenized to reduce the droplet size to $D_{90}$ particle size of about 250 nm with the help of high pressure homogenization to get the nano emulsion. The aqueous dispersion of Carbopol 980 was mixed with nano emulsion to get followed by the addition of Sodium Hydroxide Solution to form a lotion.

EXAMPLE 7

Clobetasol Propionate and Salicylic Acid Lotion

TABLE 7

| Ingredients | % w/w |
|---|---|
| Clobetasol Propionate | 0.001-0.1 |
| Salicylic Acid | 4-8 |
| Lactic Acid | 1-5 |
| Polysorbate 80 | 1-5 |
| Alcohol | 3-7 |
| Glycerine | 3-7 |
| Soyabean Oil | 7-10 |
| BHT | 0.005-0.5 |
| Carbopol 980 | 2-5 |
| Sodium Hydroxide | Q.S |
| Purified Water | Q.S |

Procedure: Clobetasol Propionate and BHT were dissolved with alcohol, salicylic acid, sodium hydroxide, water, polysorbate 80, glycerine and soyabean oil. The resulting blend was homogenized to reduce the droplet size to $D_{90}$ particle size of about 250 nm by pressure homogenization to get the nano emulsion. The aqueous dispersion of Carbopol 980 and lactic acid was mixed with nano emulsion followed by the addition of Sodium Hydroxide solution to get to form a lotion.

EXAMPLE 8

Clobetasol Propionate and Salicylic Acid Lotion

TABLE 8

| Ingredients | % w/w |
| --- | --- |
| Clobetasol Propionate | 0.01-0.1 |
| Salicylic Acid | 4-8 |
| Lactic Acid | 1-5 |
| Polysorbate 80 | 1-5 |
| Alcohol | 3-7 |
| Glycerine | 3-7 |
| Soyabean Oil | 7-10 |
| BHT | 0.001-0.5 |
| Carbopol 980 NF | 0.5-4 |
| HEC (250 HHX) | 0.5 |
| Sodium Hydroxide I.P. | Q.S |
| Purified Water IP | Q.S |

Procedure: Clobetasol propionate and BHT were mixed with alcohol, salicylic acid, sodium hydroxide, water, polysorbate 80, glycerine and soyabean oil. The resulting blend was homogenized to reduce the droplet size to $D_{90}$ particle size of about 250 nm by high pressure homogenization to get the nano emulsion. Sodium Hydroxide solution was added to aqueous dispersion of lactic acid and HEC to adjust the desired pH. This aqueous dispersion of HEC was then mixed with nano emulsion to form a lotion.

EXAMPLE 9

Clobetasol Propionate and Salicylic Acid Nanogel

TABLE 9

| Ingredients | % w/w |
| --- | --- |
| Clobetasol Propionate | 0.01-0.1 |
| Salicylic Acid | 3-8 |
| Polysorbate 80 | 1-5 |
| Alcohol | 3-7 |
| Glycerine | 3-7 |
| Soyabean Oil | 7-12 |
| BHT | 0.001-0.5 |
| Carbopol 980 | 1-4 |
| Sodium Hydroxide | Q.S |
| Purified Water | Q.S |

Procedure: Clobetasol propionate and BHT were mixed with Alcohol, salicylic acid, sodium hydroxide, water, polysorbate 80, glycerine and soyabean oil. The resulting blend was homogenized to reduce the droplet size to $D_{90}$ particle size of about 250 nm by high pressure homogenization to get the nano emulsion. Sodium Hydroxide solution was added to aqueous dispersion of Carbopol 980 to adjust the desired pH. This aqueous dispersion of Carbopol 980 was then mixed with nano emulsion to get nanogel.

EXAMPLE 10

Stability Study on Nanogel Composition of Example 1

TABLE 10

| | % Drug in the formulation | | | |
| --- | --- | --- | --- | --- |
| Drug/Property | Initial | 1 Month | 2 Month | 3 Month |
| Clobetasol | 100.9 | 98.5 | 100.6 | 97.2 |
| Salicylic acid | 100.6 | 102.8 | 101.7 | 105.9 |
| pH | 5.87 | 5.89 | 5.68 | 5.143 |

Table 10 provides stability data of nanogel composition of Example 1 when stored at 40° C. and 75% relative humidity for three months and indicates that said compositions remains stable and retains at least 80% potency of clobetasol and salicylic acid over the storage period.

EXAMPLE 11

Stability Study on Nanogel Composition of Example 2

TABLE 11

| | % Drug in the formulation | | | |
| --- | --- | --- | --- | --- |
| Drug/Property | Initial | 1 Month | 2 Month | 3 Month |
| Clobetasol | 100.1 | 97.4 | 100.3 | 98.5 |
| Salicylic acid | 100.1 | 101.5 | 100.1 | 104.1 |
| pH | 5.88 | 5.94 | 5.96 | 5.16 |

Table 11 provides stability data of nanogel composition of Example 2 when stored at 40° C. and 75% relative humidity for three months and indicates that said compositions remains stable and retains at least 80% potency of clobetasol and salicylic acid over the storage period.

We claim:
1. A stable topical pharmaceutical composition comprising:
 (a) 0.01-0.5% clobetasol or a salt or ester thereof;
 (b) 4-8% salicylic acid
 (c) 1-5% lactic acid
 (d) 1-5% polyoxyethylene (20) sorbitan monooleate
 (e) 3-7% of alcohol
 (f) 3-7% of lipids
 (g) 7-12% of oils
 (h) 0.05-0.5% of butylated hydroxytoluene
 (i) 0.5-3% a carbomer
 (j) one or more pH adjusting agents, and
 (k) water;
 wherein the composition comprises a particle size of about 250 nm and a pH of about 5.87.
2. The composition of claim 1, wherein the composition retains at least 80% potency of the clobetasol or a salt or ester thereof after storage for 3 months at 40° C. and 75% relative humidity.
3. The composition of claim 1, wherein the composition is in the form of a cream, an ointment, a gel, a lotion, liniment, paste or an emulsion.

4. A stable topical pharmaceutical composition comprising:
(a) 0.01-0.5% of clobetasol or a salt or ester thereof;
(b) 3-8% salicylic acid
(c) 1-5% lactic acid
(d) 1-5% Polyoxyethylene (20) sorbitan monooleate
(e) 3-7% of alcohol
(f) 3-7% of lipids
(g) 7-10% of oils
(h) 0.001-0.5% of butylated hydroxytoluene
(i) 0.5-3% hydroxyethylcellulose
(j) one or more pH adjusting agents, and
(k) water;
wherein the composition comprises a particle size of about 250 nm and a pH of about 5.88.

5. The composition of claim 4, wherein the composition retains at least 80% potency of the clobetasol and salicylic acid or a salt or ester thereof after storage for 3 months at 40° C. and 75% relative humidity.

6. A method of treating psoriasis, the method comprising administering the stable topical pharmaceutical composition of claim 1.

7. A method of treating psoriasis, the method comprising administering the stable topical pharmaceutical composition of claim 4.

* * * * *